United States Patent
Criscione et al.

(10) Patent No.: US 9,833,551 B2
(45) Date of Patent: Dec. 5, 2017

(54) FULLY IMPLANTABLE DIRECT CARDIAC AND AORTIC COMPRESSION DEVICE

(71) Applicants: THE TEXAS A&M UNIVERSITY SYSTEM, College Station, TX (US); CorInnova Incorporated, Houston, TX (US)

(72) Inventors: John C. Criscione, College Station, TX (US); Boris Leschinsky, Mahwah, NJ (US)

(73) Assignees: The Texas A&M University System, College Station, TX (US); Corinnova Incorporated, Houston, TX (US)

( * ) Notice: Subject to any disclaimer, the term of this patent is extended or adjusted under 35 U.S.C. 154(b) by 0 days.

(21) Appl. No.: 15/140,058

(22) Filed: Apr. 27, 2016

(65) Prior Publication Data
US 2016/0317729 A1 Nov. 3, 2016

Related U.S. Application Data

(60) Provisional application No. 62/154,195, filed on Apr. 29, 2015.

(51) Int. Cl.
*A61N 1/362* (2006.01)
*A61M 1/10* (2006.01)
(Continued)

(52) U.S. Cl.
CPC .......... *A61M 1/1068* (2013.01); *A61M 1/107* (2013.01); *A61N 1/0597* (2013.01);
(Continued)

(58) Field of Classification Search
CPC .............. A61M 1/1072; A61M 1/1068; A61M 1/1044; A61M 1/1063; A61M 1/122;
(Continued)

(56) References Cited

U.S. PATENT DOCUMENTS

| 2,826,193 A | 3/1958 | Vineberg |
| 3,034,501 A | 5/1962 | Hewson |
| (Continued) | | |

FOREIGN PATENT DOCUMENTS

| WO | 9922784 A1 | 5/1999 |
| WO | 0036995 A2 | 6/2000 |
| (Continued) | | |

OTHER PUBLICATIONS

Anstadt, et al., "Non-blood contacting biventricular support for severe heart failure." Ann Thorac Surg (2002), 73:556-62.
(Continued)

*Primary Examiner* — Robert N Wieland
(74) *Attorney, Agent, or Firm* — Chainey P. Singleton

(57) ABSTRACT

The present invention provides a combined direct cardiac compression and aortic counterpulsation device comprising: an inflatable direct cardiac compression jacket configured when inflated to directly compress a heart and assist in displacing blood therefrom, an aortic counterpulsation chamber configured when inflated to displace aortic volume for the purposes of causing a counterpulsation effect, and a driver operably connected to said inflatable direct cardiac compression jacket and to said aortic counterpulsation chamber, said driver is configured to inflate said direct cardiac compression jacket and to deflate said aortic counterpulsation chamber during systole of the heart; said driver is further configured to deflate said direct cardiac compression jacket and to inflate said aortic counterpulsation chamber during diastole of the heart.

17 Claims, 9 Drawing Sheets

(51) Int. Cl.
  *A61N 1/05* (2006.01)
  *A61N 1/39* (2006.01)
  *A61M 1/12* (2006.01)
  *A61B 5/00* (2006.01)

(52) U.S. Cl.
  CPC ............ *A61N 1/3962* (2013.01); *A61B 5/686* (2013.01); *A61B 5/6869* (2013.01); *A61B 5/6876* (2013.01); *A61F 2250/0067* (2013.01); *A61M 1/106* (2013.01); *A61M 1/1067* (2013.01); *A61M 1/12* (2013.01); *A61M 1/122* (2014.02); *A61M 2205/054* (2013.01)

(58) Field of Classification Search
  CPC ... A61M 1/107; A61N 1/0597; A61N 1/3962; A61B 5/686; A61B 5/6869; A61B 5/6876
  See application file for complete search history.

(56) References Cited

U.S. PATENT DOCUMENTS

| | | |
|---|---|---|
| 3,233,607 A | 2/1966 | Bolie |
| 3,513,836 A | 5/1970 | Sausse |
| 4,048,990 A | 9/1977 | Goetz |
| 4,185,617 A | 1/1980 | Hutchins |
| 4,536,893 A | 8/1985 | Parravicini |
| 4,685,446 A | 8/1987 | Choy |
| 5,089,017 A | 2/1992 | Young et al. |
| 5,119,804 A | 6/1992 | Anstadt |
| 5,131,905 A | 7/1992 | Grooters |
| 5,169,381 A | 12/1992 | Snyders |
| 5,256,132 A | 10/1993 | Snyders |
| 5,273,518 A * | 12/1993 | Lee ................... A61M 1/1068 600/16 |
| 5,348,528 A | 9/1994 | Vince |
| 5,429,584 A * | 7/1995 | Chiu .................... A61M 1/106 600/18 |
| 5,483,958 A | 1/1996 | Merberg et al. |
| 5,562,730 A | 10/1996 | Davidson |
| 5,627,630 A | 5/1997 | Matsumae et al. |
| 5,713,954 A | 2/1998 | Rosenberg et al. |
| 5,738,627 A | 4/1998 | Kovacs et al. |
| 5,749,839 A | 5/1998 | Kovacs |
| 5,863,574 A | 1/1999 | Julien |
| 6,155,968 A | 12/2000 | Wilk |
| 6,224,540 B1 | 5/2001 | Lederman et al. |
| 6,293,906 B1 | 9/2001 | Vanden Hoek et al. |
| 6,387,042 B1 | 5/2002 | Herrero |
| 6,540,666 B1 | 4/2003 | Chekanov |
| 6,592,619 B2 | 7/2003 | Melvin |
| 6,595,912 B2 | 7/2003 | Lau et al. |
| 6,602,182 B1 | 8/2003 | Milbocker |
| 6,602,184 B2 | 8/2003 | Lau et al. |
| 6,612,978 B2 | 9/2003 | Lau et al. |
| 6,612,979 B2 | 9/2003 | Lau et al. |
| 6,626,821 B1 | 9/2003 | Kung et al. |
| 6,663,558 B2 | 12/2003 | Lau et al. |
| 6,685,627 B2 | 2/2004 | Jayaraman |
| 6,723,039 B2 | 4/2004 | French et al. |
| 6,784,283 B2 | 8/2004 | Andersen et al. |
| 7,097,611 B2 | 8/2006 | Lau et al. |
| 7,229,405 B2 | 6/2007 | Lau et al. |
| 7,275,542 B2 | 10/2007 | Lurie et al. |
| 7,445,593 B2 | 11/2008 | Criscione |
| 7,489,380 B2 | 2/2009 | Lim et al. |
| 7,494,459 B2 | 2/2009 | Anstadt et al. |
| 7,674,222 B2 | 3/2010 | Nikolic et al. |
| 7,871,366 B2 | 1/2011 | Criscione et al. |
| 7,935,045 B2 | 5/2011 | Criscione et al. |
| 8,011,367 B2 | 9/2011 | Lurie et al. |
| 8,075,471 B2 | 12/2011 | Trumble |
| 8,187,160 B2 | 5/2012 | Criscione et al. |
| 8,192,351 B2 | 6/2012 | Fishler et al. |
| 8,550,976 B2 | 10/2013 | Criscione |
| 8,944,986 B2 | 2/2015 | Altman et al. |
| 9,259,520 B2 | 2/2016 | Altman et al. |
| 2002/0007216 A1 | 1/2002 | Melvin |
| 2002/0065449 A1 | 5/2002 | Wardle |
| 2003/0088151 A1 | 5/2003 | Kung et al. |
| 2004/0010180 A1 | 1/2004 | Scorvo |
| 2005/0004420 A1 | 1/2005 | Criscione |
| 2005/0187425 A1 | 8/2005 | Alferness et al. |
| 2005/0217677 A1 | 10/2005 | Lurie et al. |
| 2006/0241334 A1 | 10/2006 | Dubi et al. |
| 2006/0276683 A1 | 12/2006 | Feld et al. |
| 2006/0287568 A1 | 12/2006 | Jassawalla et al. |
| 2007/0015958 A1 | 1/2007 | Lau et al. |
| 2007/0016184 A1 | 1/2007 | Cropper et al. |
| 2007/0161846 A1 | 7/2007 | Nikolic et al. |
| 2007/0208214 A1 | 9/2007 | Hjelle et al. |
| 2007/0221222 A1 | 9/2007 | Lurie |
| 2007/0276444 A1 | 11/2007 | Galbart et al. |
| 2008/0004488 A1 | 1/2008 | Hjelle et al. |
| 2008/0021260 A1 | 1/2008 | Criscione et al. |
| 2008/0021266 A1 | 1/2008 | Laham et al. |
| 2008/0071134 A1 | 3/2008 | Dubi et al. |
| 2008/0257344 A1 | 10/2008 | Lurie et al. |
| 2009/0036730 A1 | 2/2009 | Criscione et al. |
| 2009/0043152 A1 | 2/2009 | Lau et al. |
| 2009/0062701 A1 | 3/2009 | Yannopoulos et al. |
| 2009/0118570 A1 | 5/2009 | Harrison et al. |
| 2009/0318746 A1 | 12/2009 | Thurmond, II et al. |
| 2010/0081867 A1 | 4/2010 | Fishler et al. |
| 2010/0152531 A1 | 6/2010 | Goodman et al. |
| 2010/0249519 A1 | 9/2010 | Park et al. |
| 2011/0021864 A1 | 1/2011 | Criscione et al. |
| 2011/0034776 A1 | 2/2011 | Dixon et al. |
| 2011/0040152 A1 | 2/2011 | Kim et al. |
| 2011/0166410 A1 | 7/2011 | Gutierrez et al. |
| 2013/0102849 A1 | 4/2013 | Criscoine et al. |
| 2013/0150923 A1 | 6/2013 | Schnetz et al. |
| 2014/0194671 A1 | 7/2014 | Wildhirt |
| 2015/0165104 A1 | 6/2015 | Criscione et al. |

FOREIGN PATENT DOCUMENTS

| | | |
|---|---|---|
| WO | 03001971 A2 | 1/2003 |
| WO | 2004112867 A1 | 12/2004 |
| WO | 2006108177 A2 | 10/2006 |
| WO | 2007062239 A2 | 5/2007 |
| WO | 2008154033 A2 | 12/2008 |
| WO | 2009018358 A2 | 2/2009 |
| WO | 2011011641 A2 | 1/2011 |
| WO | 2011011642 A2 | 1/2011 |
| WO | 2012000003 A1 | 1/2012 |
| WO | 2012075460 A2 | 6/2012 |
| WO | 2012094064 A1 | 7/2012 |
| WO | 2013059316 A2 | 4/2013 |
| WO | 2014030140 A1 | 2/2014 |

OTHER PUBLICATIONS

Artrip, et al., "Physiological and hemodynamic evaluation of non-uniform direct cardiac compression." Circulation (1999), 100 (suppl II):236-43.

Cohn, et al. "Cardiac Remodeling—Concepts and Clinical Implications: A Consensus Paper From an International Forum on Cardiac Remodeling" Journal of the American College of Cardiology vol. 35, No. 3, Mar. 1, 2000.

Cooley, et al. "The past 50 years of cardiovascular surgery" (2000) Circulation 102: IV88-93.

Dipla, et al., "Myocyte Recovery After Mechanical Circulatory Support in Humans with End-stage Heart Failure." Circulation (1998), 97:2316-2322.

European Patent Office, Partial Supplementary European Search Report for EP 12841226.9 (PCT/US2012/060609), dated Jun. 9, 2015.

European Patent Office, European Search Report for EP 12841226.9 (PCT/US2012/060609), dated Dec. 14, 2015.

Feldman, et al. "Selective Changes in Cardiac Gene Expression During Compensated Hypertrophy and the Transition to Cardiac

(56) References Cited

OTHER PUBLICATIONS

Decompensation in Rats with Chronic Aortic Banding" (Jul. 1993). Circ. Res. 73: 184-192.

Ghanta, et al, "Adjustable, Physiological Ventricular Restraint Improves Left Ventricular Mechanics and Reduces Dilation in an Ovine Model of Chronic Heart Failure," Mar. 13, 2007, Circuilation (10):12-1-10.

Ghanta, et al, "Real-time Adjustment of Ventricular Restraint Therapy in Heart Failure," Dec. 2008, Eur. J. Cardiothorac Surg., 34(6):1136-40, available online Aug. 19, 2008.

Gheorhiad, et al. "Chronic heart failure in the united states: a manifestation of coronary artery disease" (1998) Circulation 97:282-9.

Goldstein, et al., "Medical progress: implantable left ventricular assist devices." N Engl J Med (Nov. 19, 1998), 339 (21):1522-1533.

Heerdt, et al., "Chronic Unloading by Left Ventricular Assist Device Reverses Contractile Dysfunction and Alters Gene Expression in End-Stage Heart Failure." Circulation (2000), 102:2713-2719.

Karvarana, et al., "Circulatory support with a direct cardiac compression device: a less invasive approach with the AbioBooster device." J Thorac Cardiovasc Surg, (Oct. 2001), 122:786-787.

Kawaguchi, et al., "Mechanical enhancement of myocardial oxygen saving by synchronized dynamic left ventricular compression." J Thorac Cardiovasc Surg (1992), 103:573-81 (Abstract Only).

Kherani, et al., "Ventricular Assist Devices as a Bridge to Transplant or Recovery." Cardiol (2004), 101:93-103.

Machine Translation of WO 2012/000003 (PCT/AT2011/000218)—Publication date Jan. 5, 2012—Abstract, description & claims, 21 pp.

Mann, et al, "Mechanisms and Models in Heart Failure: the Biomechanical Model and Beyond," May 31, 2005, Circulation, 111(21):2837-49.

Mann, et al, "Left Ventricular Size and Shape: Determinants of Mechanical Signal Transduction Pathways," 2005, Heart Failure Reviews, vol. 10, No. 2, pp. 95-100.

Moreno, et al, "Assessment of Minimally Invasive Device That Provides Simultaneous Adjustable Cardiac Support and Active Synchronous Assist in an Acute Heart Failure Model," Journal of Medical Devices, Dec. 2011, vol. 5 / 041008-1.

Omens, J.H. "Stress and strain as regulators of myocardial growth." Prog. Biophys. Molec. Biol. (1998), 69:559-572.

Oz, et al., "Direct Cardiac Compression Devices." J Heart Lung Transplant (Oct. 2002), 21:1049-1055.

Rose, et al., "Long-Term Use of Left Ventricular Assist Device for End-stage Heart Failure." N Engl J Med (Nov. 15, 2001), 345(20):1435-1443.

Snowden, et al. "Modulation of Diastolic Filling Using an Epicardial Diastolic Recoil Device" Journal of Medical Devices Sep. 2013, vol. 7 / 034503-1.

Tamminen, et al., "Ectopic Expression of AB13 Gene Enhances Freezing Tolerance in Response to Abscisic Acid and Low Temperature in Arabidopsis Thaliana," The Plant Journal, (2001), 25(1):1-8.

Williams, et al. "Direct cardiac compression for cardiogenic shock with the CardioSupport System." Ann Thorac Surg (2001), 71:S188-9.

United States Patent & Trademark Office (ISA), International Search Report and Written Opinion for PCT/US2005/003343 dated Jul. 16, 2007.

European Patent Office, Supplementary European Search Report for EP 10802924.0 (PCT/US2010/042970), dated Sep. 27, 2012.

European Patent Office (ISA), Written Opinion for PCT/US2004/019809 dated Oct. 24, 2005—8 pp.

Korean Intellectual Property Office (ISA), International Search Report for PCT/US2010/042970, dated May 2, 2011, 13 pp.

Korean Intellectual Property Office (ISA), International Search Report and Written Opinion for PCT/US2010/042972, dated Apr. 14, 2011, 8 pp.

Korean Intellectual Property Office (ISA), International Search Report for PCT/US2008/071618 dated Feb. 12, 2009.

Korean Intellectual Property Office (ISA), International Search Report and Written Opinion for PCT/US2011/063178 dated Jun. 25, 2012—14 pp.

Korean Intellectual Property Office (ISA), International Search Report and Written Opinion for PCT/US2012/060609 dated Apr. 19, 2013—15 pp.

United States Patent & Trademark Office (ISA) (Corrected), International Search Report and Written Opinion for PCT/US2006/013457 dated Dec. 10, 2007.

United States Patent & Trademark Office (ISA), International Search Report and Written Opinion for PCT/US2016/029756 dated Jul. 27, 2016.

United States Patent & Trademark Office (ISA), International Search Report and Written Opinion for PCT/US2016/042578 dated Oct. 19, 2016.

\* cited by examiner

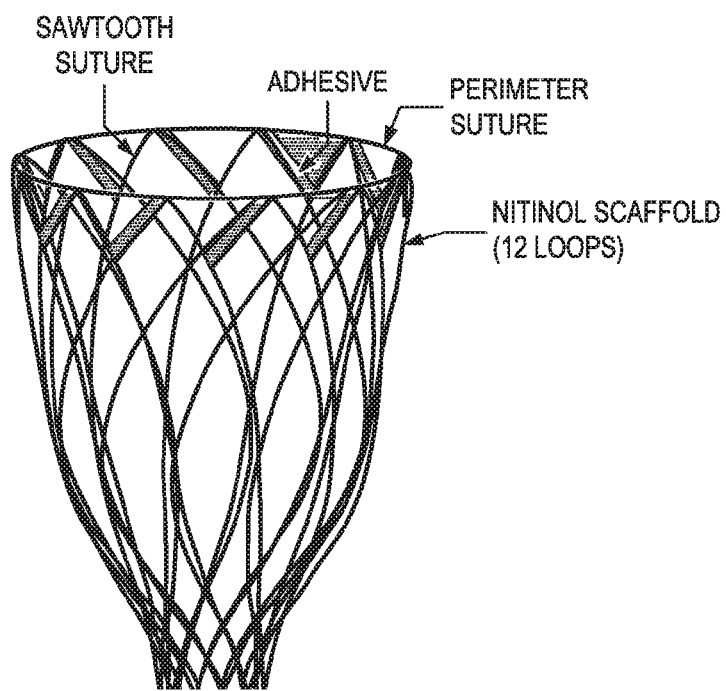
FIG. 7
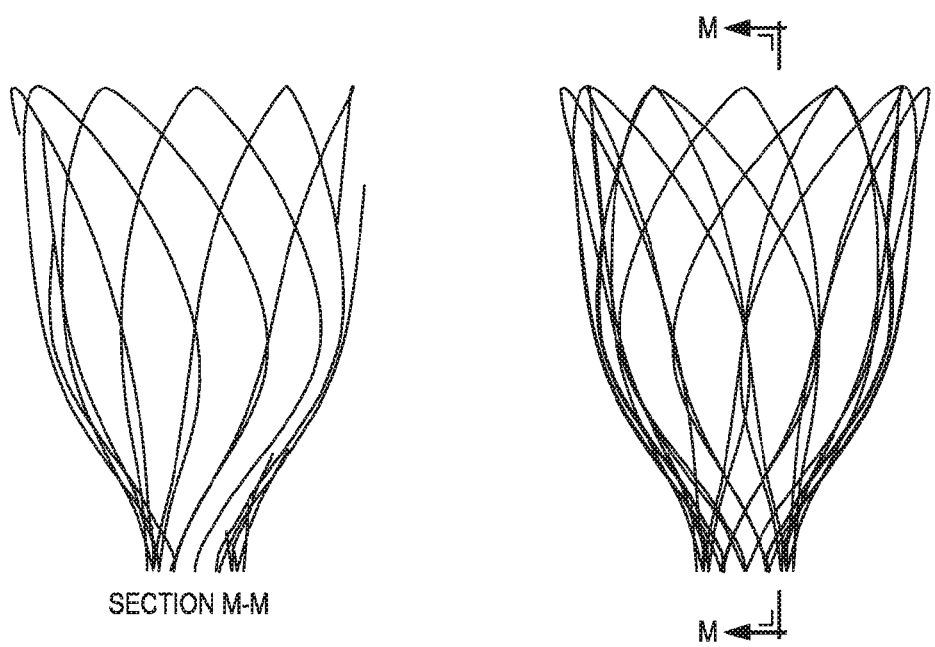
FIG. 8A
FIG. 8B

FULLY IMPLANTABLE DIRECT CARDIAC AND AORTIC COMPRESSION DEVICE

CROSS-REFERENCE TO RELATED APPLICATIONS

This application claims benefit of U.S. Provisional Application Ser. No. 62/154,195 filed Apr. 29, 2015 which is incorporated herein by reference in its entirety.

TECHNICAL FIELD OF THE INVENTION

The present invention relates in general to the field of heart assist devices, and more particularly, to a fully implantable device for direct cardiac compression and aortic compression.

STATEMENT OF FEDERALLY FUNDED RESEARCH

Not applicable.

INCORPORATION-BY-REFERENCE OF MATERIALS FILED ON COMPACT DISC

Not applicable.

BACKGROUND OF THE INVENTION

Without limiting the scope of the invention, its background is described in connection with a fully implantable device for direct cardiac compression and aortic compression. During a cardiac cycle, the heart expels oxygenated blood into the aorta as its left ventricle contracts (i.e., during systole) and, thereafter, receives a backflow of arterial blood into the coronary arteries as its left ventricle relaxes (i.e., during diastole). The systolic pumping of blood into the aorta requires the myocardium to overcome the static pressure of blood that is already in the aorta. A healthy heart is typically able to perform both of these functions effectively. However, a weakened or failing heart may be unable to perform the work required to fully overcome the static pressure of blood already in the aorta, thereby resulting in less ejection of oxygenated blood into the aorta during systole and less backflow of oxygenated blood into the coronary arteries during diastole. There are various methods of providing assistance to the failing myocardium.

Direct cardiac compression devices are generally known as disclosed first by Anstadt and later by Criscione and are effective in providing assistance to the failing myocardium by generally adding external pressure to help the heart muscle to contract. Generally these devices include a jacket positioned around the heart and containing inflatable bladders that are inflated to coincide with contraction of the myocardium during systole. Operation of such device is supported by a driver configured to inject fluid through a drive line to cause the bladders to expand and withdrawal of fluid during diastole causes the bladders to collapse in preparation for the next systole of the heart. The presence of the drive line exiting the subject is generally undesirable as it may be a source of infection, especially for patients requiring long-term or permanent support. One difficulty associated with injecting and removing a certain volume of drive fluid is the changing volume of the drive system. This changing volume of the drive system makes an implantable driver with changing internal volume problematic, due to the positioning of the device inside the subject so as to not periodically compress surrounding tissues.

In addition, counterpulsation devices are generally known to include an external pneumatically driven intra-aortic balloon pump that drives gas to and from an intra-aortic balloon. Implantable systems are also known and include an external aortic compression chamber attached to the ascending aorta where an injection of the drive fluid inside the chamber causes the aorta to compress, while withdrawal of drive fluid causes the aorta to relax to create a counterpulsation effect. Other implantable systems include an expandable chamber surgically attached to the descending aorta of the subject to cause its compression and expansion upon respective injection and withdrawal of the drive fluid by a fluid driver. The timing of inflation and deflation of a counterpulsation device is aligned with the diastole of the heart: the device is inflated at onset of diastole and deflated prior to or at systole.

U.S. Pat. No. 7,766,813 entitled, "Methods, devices and systems for counterpulsation of blood flow to and from the circulatory system," discloses counterpulsation methods and systems for assisting the heart of a patient involve, for example, coordinating the operation of a pulsatile pump to suction blood from an artery through a first conduit while the heart is in systole and expel the blood into the first conduit and the artery while the heart is in diastole, the entire contents of which are incorporated herein by reference.

U.S. Pat. No. 7,347,811 entitled, "Heart assist device utilizing aortic deformation," discloses providing counterpulsation heart assist by deforming the aorta, the entire contents of which are incorporated herein by reference. The deformation pressure is applied by cyclically, preferably in synchrony with the diastolic period of the heart. The deformation pressure may be applied to the outer wall of the aorta or to a patch covering a resected opening in the wall of the aorta.

U.S. Pat. No. 8,444,545 entitled, "Dual-pulsation bi-ventricular assist device," discloses a ventricular assist device which comprises a sac for wrapping around a portion of a heart, the sac having one or more inflatable chambers for compressing the heart when the chambers being inflated and a blood outlet made to an aorta, the blood outlet being the sole opening in the human blood path in the vicinity of heart, wherein during a systolic phase the inflatable chambers inflate while blood flows out of the aorta through the blood outlet, and during a diastolic phase the inflatable chambers deflate while blood flows into the aorta through the blood outlet, the entire contents of which are incorporated herein by reference.

U.S. Pat. No. 4,813,952 entitled, "Cardiac Assist Device," discloses a muscle-powered pump to assist the natural heart, the entire contents of which are incorporated herein by reference. The device comprises an oblate, spheroidal-shaped pumping chamber surrounded by innervated muscular tissue. The device may be coupled to the ventricle and descending aorta with valves and be stimulated in synchrony with the natural depolarization of the heart or the device may be inserted into the descending aorta and used as a counterpulsation device. In this application, the innervated muscle is stimulated after a brief delay from the natural cardiac depolarization.

Another device that may be used to increase myocardial blood flow in patients whose cardiac output is compromised due to heart failure or cardiac insufficiency and decreases the workload of the heart, through counterpulsation is an intra-aortic balloon pump. Intra-aortic balloon counterpulsation is a technique which causes more arterial blood to enter the coronary arteries (and thus more blood flow to the myocardium) during diastole (less flow work) and decreases the amount of work that the heart must perform during systole (less pressure work). By increasing coronary blood flow, the myocardium receives more oxygen, thereby allowing the heart to pump more effectively and increasing the cardiac output that occurs with each heartbeat (i.e., the "stroke volume"). The intra-aortic balloon counterpulsation comprises a balloon catheter that is percutaneously insertable into the aorta and a control console that is attached to the balloon catheter. A computer or controller within the control console receives the patient's electrocardiogram and causes the intra-aortic balloon to be inflated during diastole (when the heart muscle relaxed) resulting in increased back pressure within the aorta and increased blood flow into the coronary arteries, and deflated during early systole (during a phase known as "isometric contraction") resulting in a reduction of intra-aortic pressure against which the heart must pump. In this way, the intra-aortic balloon pump improves blood flow to the heart muscle and reduces the workload of the heart muscle. Additionally, intra-aortic balloon pump counterpulsation has been demonstrated to improve peripheral or systemic arterial perfusion. Although the mechanism by which intra-aortic balloon pump counterpulsation improves peripheral or systemic profusion is not well understood, it is believed that inflation of the intra-aortic balloon during diastole serves to facilitate peripheral runoff (sometimes referred to as the intrinsic "Windkessel" effect) which then augments peripheral perfusion.

SUMMARY OF THE INVENTION

The present inventors recognized a long felt but unresolved need for a device with maximal degree of assistance to the heart and the circulatory system that uses a fully implantable driver so as to minimize the risk of infection when such device is used over an extended period-of-time.

The present invention provides a combined direct cardiac compression and aortic counterpulsation device comprising: an inflatable direct cardiac compression jacket configured when inflated to directly compress a heart and assist in displacing blood therefrom, an aortic counterpulsation chamber configured when inflated to displace aortic volume for the purposes of causing a counterpulsation effect, and a driver operably connected to said inflatable direct cardiac compression jacket and to said aortic counterpulsation chamber, said driver is configured to inflate said direct cardiac compression jacket and to deflate said aortic counterpulsation chamber during systole of the heart; said driver is further configured to deflate said direct cardiac compression jacket and to inflate said aortic counterpulsation chamber during diastole of the heart.

The present invention provides a combined direct cardiac compression and aortic counterpulsation device comprising: an inflatable direct cardiac compression jacket configured when inflated to directly compress an external surface of a heart and assist in displacing blood therefrom, an aortic counterpulsation chamber configured when inflated to displace aortic volume for the purposes of causing a counterpulsation effect, and a driver operably connected to said inflatable direct cardiac compression jacket and to said aortic counterpulsation chamber, said driver is configured to shuttle a drive fluid back and forth between said direct cardiac compression jacket and said aortic counterpulsation chamber to alternate inflations and deflations thereof.

The present invention provides a combined direct pulsation and counterpulsation device comprising: a first inflatable component in direct contact with a heart, a second inflatable component in direct contact with at least one great artery, a driver operably connected to said first and second inflatable components, wherein said device is configured to fill said first inflatable component with fluid at least partially removed from said second inflatable component during systolic ejection by the heart; said device is further configured to fill said second inflatable component with fluid at least partially removed from said first inflatable component during diastolic filling of the heart.

The present invention provides a combined direct cardiac compression and aortic counterpulsation device comprising: an inflatable direct cardiac compression device comprising a resilient inner panel in contact with a heart periphery comprising two or more membranes contoured to provide curvatures generally in the shape of the heart to supply resistance to the movement of the heart to affect the end-diastolic heart volume, an inflatable outer panel comprising one or more inflatable membranes positioned at least partially around the resilient inner panel to inflate and provide resistance to the movement of the heart to affect the end-systolic heart volume, and one or more fluid connections in communication with the inflatable outer panel for inflation and deflation; an aortic counterpulsation device, wherein the aortic counterpulsation device comprises a substantially inelastic curved shell comprising an outer surface and a substantially concave inner surface, a flexible membrane coupled to the shell to form an inflatable space there between, wherein the flexible membrane has a deflated configuration and an inflated configuration, an inlet/outlet port in fluid communication with the inflatable space, and a wrap coupled to the substantially inelastic curved shell to removeably position to hold the flexible membrane against a radially outer side of a curvature of the aorta, wherein the device has no other component or structure for holding the device against the ascending aorta, wherein the shell is configured to extend around only a portion of the circumference of the ascending aorta; and a driver operably connected to the one or more fluid connections of the inflatable direct cardiac compression device and to the aortic counterpulsation device to inflate the inflatable direct cardiac compression device and to deflate the aortic counterpulsation device during systole of the heart and to deflate the inflatable direct cardiac compression device and to inflate the aortic counterpulsation device during diastole of the heart.

BRIEF DESCRIPTION OF THE DRAWINGS

For a more complete understanding of the features and advantages of the present invention, reference is now made to the detailed description of the invention along with the accompanying figures and in which:

FIGS. 2A-2B are schematic diagrams of the cross-section, top down view, of a device according to one embodiment of the present invention without a heart inside, wherein FIG. 2A is in the deflated state and FIG. 2B is in the pressurized state;

FIGS. 3A-3B are schematic diagrams of the long-section of a device according to one embodiment of the present invention without a heart inside, wherein FIG. 3A is in the deflated state and FIG. 3B is in the pressurized state;

FIGS. 4A-4B are schematic diagrams of the cross-section of a device according to one embodiment of the present invention with a heart inside, wherein FIG. 4A is in the deflated state and FIG. 4B is in the pressurized state;

FIGS. 5A-5B are schematic diagrams of the long-section of a device according to an embodiment of the present invention with a heart inside, wherein FIG. 5A is in the deflated state and FIG. 5B is in the pressurized state;

FIG. 7 is an illustration of one embodiment of the present invention wherein a nitinol scaffold is incorporated to mediate the end-diastolic configuration;

FIGS. 8A-8B are illustrations of two views of one embodiment of the present invention wherein a nitinol scaffold is incorporated to mediate the end-diastolic configuration;

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Though different devices exist today with specific indications for medium/long term support, the present invention is a significant innovation in the cardiac device industry, as it can address both systolic and diastolic heart failure with a single device design. The present invention minimizes infection, and coagulation. Heart replacement is highly invasive and induces great trauma on the patient and complications from anti-rejection medication. Current, blood-contacting assist technologies provide greater risk factors for blood trauma, clotting activation, and sepsis. Blood-contacting assist technologies cannot be started and stopped because of clot formation. The present invention can be used in combination therapies which combine mechanical, electrical, pharmaceutical, and/or stem cell therapies.

Figure 9:
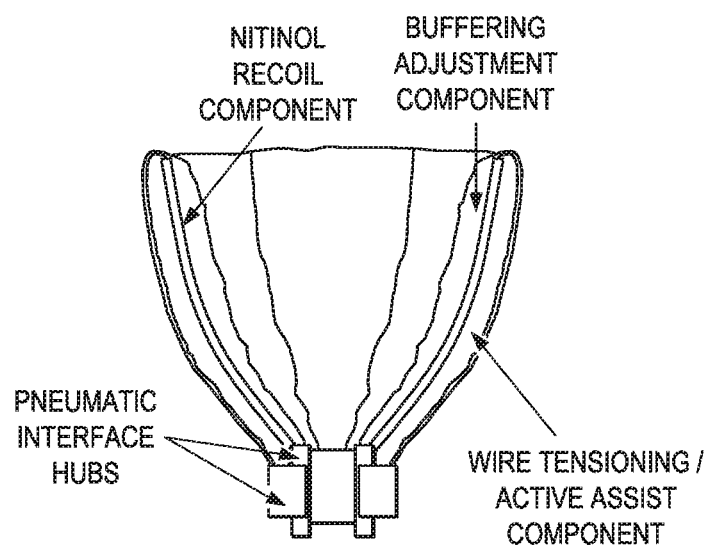
FIG. 9 is a cross-section illustration of one embodiment of the present invention depicting its support, assist, and recoil components.

The present invention provides a fully implantable device for direct cardiac compression and aortic compression. Although any direct cardiac compression device may be used in conjunction with the present invention from the Anstadt cup as illustrated in FIG. 9 of the Anstadt patent (U.S. Pat. No. 5,119,804) to a contoured diastolic recoil device as seen in U.S. Pat. No. 8,944,986 and U.S. Provisional Patent Application Ser. Nos. 61/271,559 and 61/276,215.

Figure 1A:
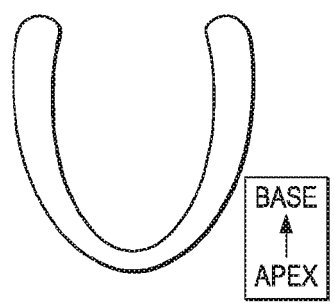
FIGS. 1A-1D are diagrams showing the normal, null and inverted curvature in apex-to-base, radial plane of the heart.
Figure 1B:
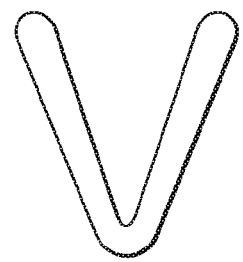
Figure 1C:
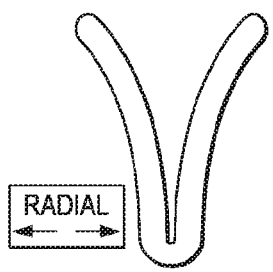
Figure 1D:
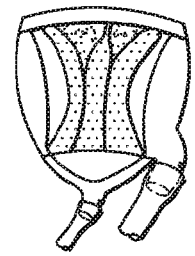

What follows is a discussion of the disadvantages of the direct cardiac compression device in the prior art. FIGS. 1A-1D show the normal, null, and inverted curvature in apex-to-base, radial plane (long axis) of the heart. FIG. 1A illustrates a normal or positive curve with the inside of the curve toward the chamber, where the top references the base and the bottom references the apex. FIG. 1B illustrates a null curvature. FIG. 1C illustrates an inverted or negative curvature where the inside of the curve is away from the chamber. FIG. 1D is an illustration that shows the curvature inversion of the Anstadt cup as illustrated in FIG. 9 of the Anstadt patent (U.S. Pat. No. 5,119,804). Direct cardiac compression devices (DCCDs) have been characterized as most promising with good hemodynamics and ease of implantation. A number of DCCDs are being developed. The Anstadt cup is shown in FIG. 1D. The CardioSupport System by Cardio Technologies Inc. is similar to the Anstadt cup. The attachment is via vacuum on the apical end and the assist is via inflation of a membrane that lies between a rigid shell and the epicardial surfaces of the right ventricle (RV) and left ventricle (LV). The devices of Parravicini and the AbioBooster by Abiomed, Inc. are sewn to the interventricular sulci, and elastic sacks between the shell and the epicardial surface are inflated during systole. The direct cardiac compression (DCC) Patch by Heart Assist Tech Pty Ltd. is similar to the AbioBooster. It has been described as " . . . two patches shaped to suit the profile of the heart . . . inflated and deflated in synchrony with the heart . . . " The heart booster is composed of longitudinal tubes that have elliptical cross-sections with the major axis of the ellipse in the hoop direction.

To understand how all of these DCCDs induce aberrant strain patterns, it is important to note that contraction strain depends on both the end-diastolic configuration (reference configuration) and the end-systolic configuration (current configuration). The strain field is a function of the gradient (with respect to reference position) of the mapping of material points from the reference configuration to the current configuration. Thus, the fact that prior DCCDs fit the diastolic configuration is inconsequential to achieving an appropriate contraction strain pattern because their end-systolic configurations are grossly aberrant. Although strains induced by such motions as torsion may not perturb the heart geometry; if the overall geometry is abnormal, then the strain must be abnormal. Unphysiological geometries are illustrated in FIGS. 1A-1D.

Generally, the curvature is inversely proportional to the radius-of-curvature and that curvature changes sign when the origin of the radius-of-curvature changes sides. As should be evident from FIG. 1D, curvature inversion can greatly increase ejection fraction (EF). However, the curvature of the ventricles in a normal heart does not invert during systole, thus, rendering such motions grossly abnormal. A healthy heart, moreover, will resist having its curvature inverted and heart function needs to decline by 30% before the effect of "non-uniform direct cardiac compression" becomes noticeable. In short, the heart resists assist when a DCCD induces aberrant strains. DCCD devices described above induce motions that are grossly abnormal. The Vineberg device inverts curvature in long axis planes and short axis planes. The Anstadt cup and Cardio-Support System invert curvature in long axis planes yet preserve curvature in the short axis planes. The AbioBooster, DCC Patch, Hewson device, and Parravicini devices pull on the interventricular sulci and push on the freewall such that the curvature will increase at the sulci and decrease on the freewalls. The Heart Booster inverts curvature in short axis planes, yet preserves curvature in the long axis planes. Because they were not designed to eliminate aberrant motions, it should not be surprising that these existing DCCDs described above induce aberrant strain patterns.

One embodiment of the DCCD used in the present invention is the Anstadt cup. Another embodiment of the DCCD includes a selectively inflatable end-systolic heart shaped bladder with one or more contoured supports configured to surround at least a portion of the heart to provide curvatures similar to the proper shape of the heart when pressurized and one or more fluid connections in communication with the selectively inflatable end-systolic heart shaped bladder for pressurization and depressurization. The one or more contoured supports form one or more inflatable compartments having an expanded curvature optimized to fit generally the proper end-systolic shape of the heart. The selectively inflatable end-systolic heart shaped bladder includes an inner membrane that is at least partially folded when depressurized; and at least partially unfolded when pressurized. In another embodiment, the selectively inflatable end-systolic heart shaped bladder includes an inner membrane that is at least partially folded when depressurized and at least partially unfolded when pressurized; and an outer membrane that is at least partially folded when depressurized; and at least partially unfolded when pressurized. Other embodiments may include various combinations thereof. The one or more contoured supports may include one or more dividers individually of similar or different materials, one or more wires individually of similar or different materials or a combination thereof to form a shape generally appropriate to the proper end-systolic shape of the heart. The selectively inflatable end-systolic heart shaped bladder includes a material that is substantially biocompatible, fluid-impermeable and substantially elastic. For example, at least a portion of the device may be made from elastomeric polyurethane, latex, polyetherurethane, polycarbonateurethane, silicone, polysiloxaneurethane, hydrogenated polystyrene-butadiene copolymer, ethylene-propylene and dicyclopentadiene terpolymer, hydrogenated poly(styrene-butadiene) copolymer, poly(tetramethyl ene-ether glycol) urethanes, poly(hexamethylenecarbonate-ethylenecarbonate glycol) urethanes and combinations thereof. The selectively inflatable end-systolic heart shaped bladder is generally collapsible when depressurized and is reinforced to resist radially outward expansion during pressurization. The device of the present invention may take many configurations depending on the particular treatment. For example, the selectively inflatable end-systolic heart shaped bladder may include 12 inflatable tapered compartments formed by the one or more contoured supports to provide an expanded curvature similar to the proper end-systolic shape of the heart; however, other embodiments may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more inflatable tapered compartments. Furthermore, the distribution of the inflatable tapered compartments may vary from the design of 4 chambers on the RV side and 8 chambers that are mostly on the LV but also overlapping the interventricular sulci. For example, the device may have 1, 2, 3, 4, 5, 6, 7, 8, 9, 10, 11, 12 or more chambers on the RV side and 1, 2, 3, 4, 5, 6, 7, 8, 9, 10, 11, 12, 13, 14, 15, 16, 17, 18, 19, 20, 21, 22, 23, 24 or more chambers that are mostly on the LV and overlapping the interventricular sulci. That chambers distribution determination for a particular application and treatment is within the scope of the skilled artisan. The inflatable tapered compartments are connected to a pneumatic pressure source through an inlet port and an outlet port. The device is inflated with a positive pressure during systole and deflated via suction during diastole. Although, other configurations and multiple connections are also possible depending on the particular application and configuration. The inlet port and an outlet port may be connected through a single connection for applying the positive pressure and the suction or negative pressure; alternatively, multiple connections may be used. In addition, the inlet port and an outlet port may be made anywhere about the boundary of the selectively inflatable end-systolic heart shaped bladder, e.g., near the base or near the apex.

One embodiment of the DCCD applies forces to the exterior, epicardial boundary of the heart to restrict inflow and modulate right flow versus left flow through the heart. The device includes a selectively inflatable end-diastolic contoured bladder having one or more contoured supports configured to releasably engage the heart. The one or more contoured supports protrude inward towards the right ventricle to decrease the end-diastolic volume of the right ventricle during diastole. The device also has an inlet connection and outlet connection in communication with the selectively inflatable end-diastolic contoured bladder to pressurize and depressurize the selectively inflatable end-diastolic contoured bladder. Residual pressure is applied about the right ventricle to not fully deflate during diastole.

Generally, the inlet line is in communication with the inlet connection to operatively expand the selectively inflatable end-diastolic contoured bladder and an outlet line is in communication with the outlet connection to operatively withdraw fluid from the selectively inflatable end-diastolic contoured bladder. This allows connection to conventional devices to apply and remove pressure or custom devices specifically for the present invention.

A method for promoting growth and remodeling of the heart is provided by the present invention. The method includes providing access to a heart of a patient and positioning a selectively inflatable end-diastolic heart shaped bladder about at least a portion of the periphery of the heart. The selectively inflatable end-diastolic heart shaped bladder is connected to a fluid source to the selectively inflatable end-diastolic heart shaped bladder to inflate with a positive pressure during systole and deflate the selectively inflatable bladder during diastole. The residual pressure is applied about the right ventricle to not fully deflate during diastole.

The DCCD as provided by the present invention applies forces to the exterior, epicardial boundary of the heart and is optimized to fit an end-systolic shaped heart geometry. The DCCD includes a selectively inflatable bladder having one or more end-systolic contoured supports configured to surround at least a portion of the periphery of the heart and provide curvatures similar to the proper end-systolic shape of the heart when the pressurizable chamber is pressurized and one or more fluid connections in communication with the selectively inflatable bladder to pressurize and depressurize the selectively inflatable bladder.

The direct cardiac compression device promotes a contraction strain pattern on a diseased or damaged heart that reduces dyskinetic or hypokinetic motions. The device includes a selectively inflatable end-systolic heart shaped bladder with one or more contoured supports configured to surround at least a portion of the heart to provide curvatures that are similar to the proper shape of the heart when pressurized. The device also includes one or more fluid connections in communication with the selectively inflatable end-systolic heart shaped bladder for pressurization and depressurization.

In another embodiment, the DCCD is a contoured diastolic recoil device that enhances diastolic recoil that does not need to be sutured or directly attached to the heart. Rather, the diastolic recoil device intrinsically attaches to the heart via pneumatic locking. In operation, there is no free air in the chest between the device and heart, so if the heart becomes smaller (due to ejection of blood), the device is pulled inward. Likewise, when the device pushes outward, it applies a suction-like traction to the heart. If free air were present in the chest, which it normally is not, the suction-like traction would draw air between the device and heart. However, with no free air, the suction traction is applied directly to the heart surface. This pneumatic locking, or intrinsic pneumatic attachment, is illustrated by analogy: it is very difficult to pull a water balloon out of a cup when they are placed inside of a bag in which the air has been evacuated (i.e., like a closed chest). After air in the mediastinum is removed, the heart and device are pneumatically locked in a co-axial configuration. The diastolic recoil device uses the intrinsic pneumatic attachment and its elastic properties to enhance the diastolic recoil of the heart. At the end of systole and the beginning of diastole the diastolic recoil device of the present invention acts like a loaded spring, applying negative pressure to the exterior epicardial surface of the heart, helping the ventricles of the heart to fill.

The adjustability of the DCCD enables cardiologists to proactively intervene in heart failure whereby specific mechanical conditions can be generated and employed to direct growth and remodeling events that are restorative and/or rehabilitative in nature. In particular, the present invention can directly shift the end-diastolic pressure volume relationship (EDPVR) to the left, i.e., toward lower volumes and reduced LV size.

Certain embodiments of the present invention can be used in conjunction with cardiac stem cell therapies. Stem cells used for cardiac regeneration therapy include but are not limited to stem cells derived from embryonic stem cells, somatic stem cells taken from bone marrow, progenitor cells from cardiac tissue, autologous skeletal myoblasts from muscle tissue, hematopoietic stem cells, mesenchymal stem cells, and endothelial precursor cells. The present invention can also be used in combination naturally occurring cardiac stem cells. Transplanted stem cells may be injected directly into cardiac tissue including, infarcted regions, cardiac scar tissue, border zones, or healthy cardiac tissue. Transplanted stem cells may also be injected systemically feeding regions of cardiac tissue and may migrate to regions of the damaged or diseased heart and engraft to regions of the damaged or diseased heart. Transplanted stem cells may also provide diffusible products to regions of the damaged or diseased heart.

To model the treatment paradigm for embodiments of the present invention and grossly estimate what driving pressures are needed, one may use Laplace's law for a spherical vessel which gives an average wall stress based on average radius, thickness, and transmural pressure difference. Because blood is nearly incompressible, flow is dominated by pressure gradients (or less accurately by pressure differences). Without loss in generality, one may define blood pressure as its difference from atmospheric pressure. Because of rarification and densification, flows in compressible fluids are mediated by both pressure gradients and absolute pressure.

Certain embodiments of the present invention can decrease RV input to compensate for the expected increase in RV output. Absent this capability, it is likely that the RV and healthy regions of the LV would atrophy due to excessive off-loading. However, certain embodiments of the present invention are ideal for weaning or gradually decreasing Pout, and the use of clenbuterol which has been shown to be useful in achieving ventricular recovery by preventing atrophy.

One embodiment of the DCCD is a soft-shelled DCCD that has inflatable, longitudinally oriented chambers that when deflated are collapsible, allowing for minimally invasive implantation. In addition, the deflated chambers are shaped and adjoined to form a structure that allows typical diastolic configurations. When pressurized the chambers push on the exterior of the heart in such a way as to induce a systolic configuration with normal curvatures.

Figure 2A:
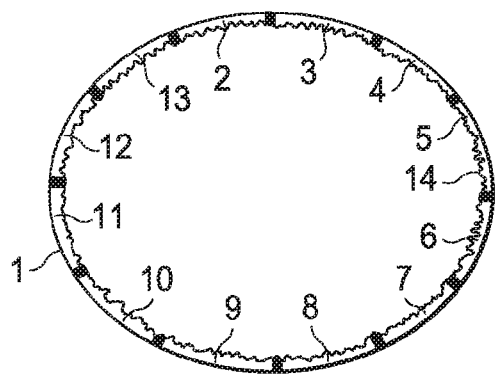
Figure 2B:
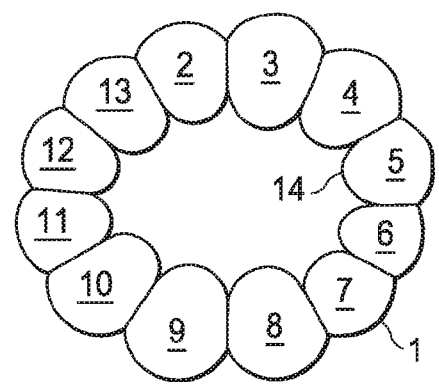

FIGS. 2A and 2B illustrate a horizontal cross section of one embodiment of the direct cardiac compression device 1 of the present invention in the deflated state, as seen in FIG. 2A and the inflated state in FIG. 2B. The direct cardiac compression device 1 includes 12 chambers 2-13 arranged with 4 chambers on the RV side and 8 chambers that are mostly on the LV but also overlapping the interventricular sulci. The chambers 2-13 are constructed from polyethylene film in one embodiment; however, other materials may be used. The side of the chambers 2-13, that are on the outer boundary, form a shape that is similar to the end diastolic shape of the heart. The interior surface 14 has folds and crenulations such that when inflated the chambers 2-13 mostly expand inward.

Figures 3A, 3B:
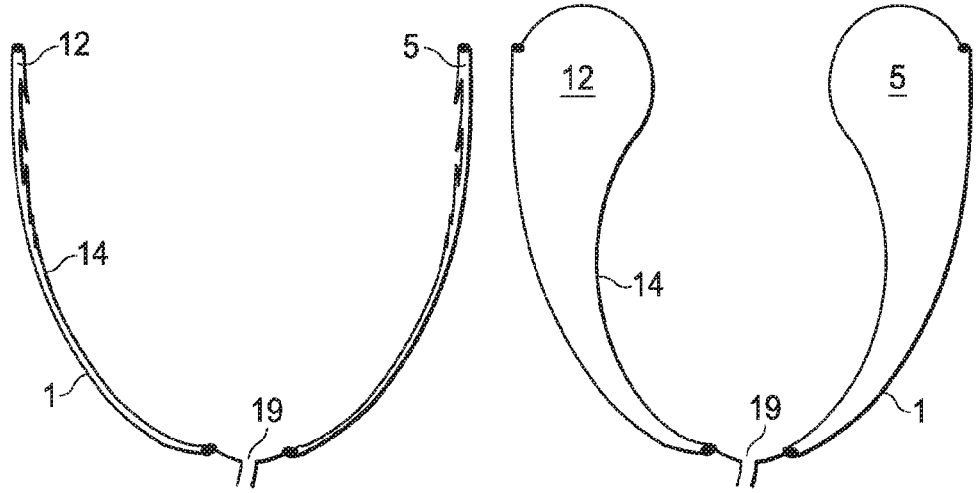

FIGS. 3A and 3B illustrate a vertical cross-section of one embodiment of the DCCD 1 of the present invention in the deflated state as seen in FIG. 3A and the inflated state in FIG. 3B. Direct cardiac compression device 1 includes chambers 5 and 12 in the inflated and deflated states using access port 19. The interior surface 14 of the chambers 2-13 that are on the outer boundary form a shape that is similar to the end diastolic shape of the heart. The interior surface 14 has folds and crenulations such that when inflated the chambers 2-13 mostly expand inward to contact the epicardium 16 of the heart 15.

Figures 4A, 4B:
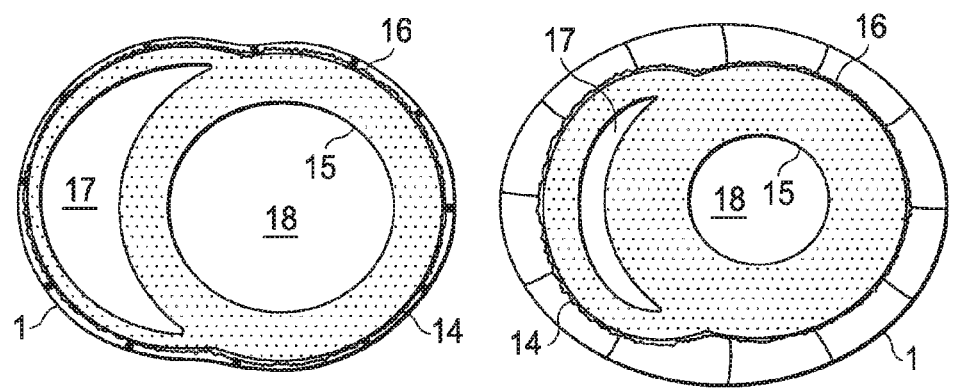

FIGS. 4A and 4B illustrate a horizontal cross-section of one embodiment of the DCCD 1 of the present invention fitted to the heart 15. FIG. 4A is in the deflated state and FIG. 4B is in the inflated state. The DCCD 1 includes 12 chambers 2-13 arranged with 4 chambers on the RV side and 8 chambers that are mostly on the LV but also overlapping the interventricular sulci. The chambers 2-13 include interior surface 14 that contacts the epicardium 16 of the heart 15. The side of the chambers 2-13 that are on the outer boundary form a shape that is similar to the end diastolic shape of the heart. The interior surface 14 has folds and crenulations such that when inflated the chambers 2-13 mostly expand inward. The shape of the interior regions of the heart 17 and 18 can be compared in the inflated state as seen in FIG. 4B and the deflated state in FIG. 4A.

Figures 5A, 5B:
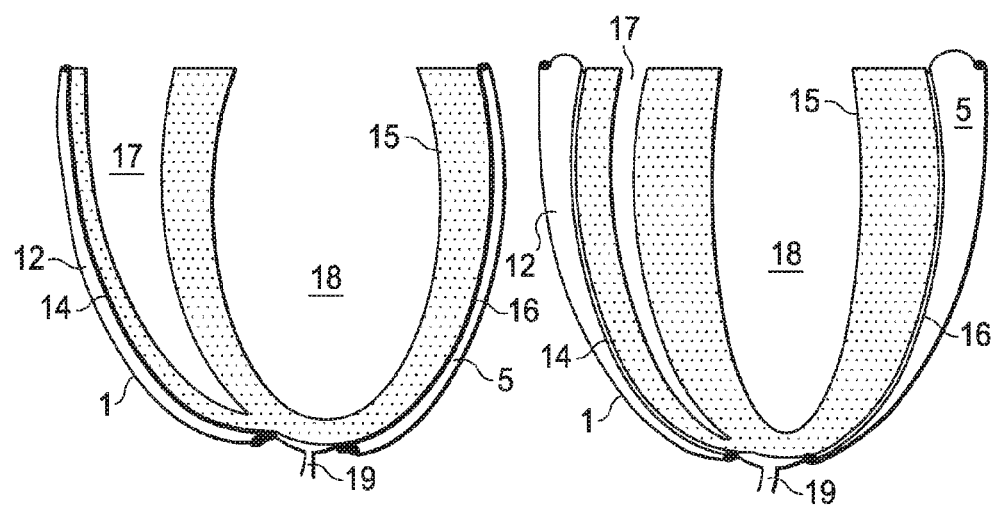

FIGS. 5A and 5B illustrate a vertical cross-section of one embodiment of the DCCD 1 fitted to the heart 15 in the deflated state as seen in FIG. 5A and the inflated state as seen in FIG. 5B. DCCD 1 includes chambers 5 and 12 in the inflated and deflated states using access port 19. The interior surface 14 of the chambers 2-13 that are on the outer boundary form a shape that is similar to the end diastolic shape of the heart. The interior surface 14 has folds and crenulations such that when inflated the chambers 2-13 mostly expand inward to contact the epicardium 16 of the heart 15. The shape of the interior regions 17 and 18 can be compared in the inflated state as seen in FIG. 5B and the deflated state as seen in FIG. 5A.

The fully pressurized shape without the heart inside is helpful for illustrating one embodiment of the present invention, yet the shape will be significantly different when the device surrounds a heart which contains blood under pressure as seen in FIGS. 2B and 4B. With a heart inside, the pressure in the lumen of the device is higher than the pressure in the inflatable chambers. Because the chambers cannot fully expand, the inner film of the chambers is not taut. Rather than being supported by tension in the film, e.g., FIG. 2B, pressure on the lumen side of the longitudinal chambers is supported by contact forces on the epicardial surface, e.g., FIG. 4B. Without tension on the inner film, the attachment points are not drawn inward, e.g., FIG. 2B. Instead, the shape of the outer sides of the chambers becomes circular to support the pressure within the chambers, e.g., FIG. 4B. Note how the inner membrane is crenulated and thus, not under tension. Consequently, the pressure in the device chambers applies direct pressure to the heart surface. In a similar manner, a blood pressure cuff applies direct pressure to the surface of a patient's arm.

Because the inflatable chambers taper as they go from base to apex in a manner that resembles natural cardiac curvature as seen in FIG. 3B, the apex of the heart will have a physiological curvature. Moreover, because the device is rigid when pressurized, the curved shape of the apical end will act to prevent the heart from being expelled from the device. Basically, for the heart to leave the device the apical shape would have to pucker or a vacuum would need to form in the apical end of the device, both of which are unlikely.

FIGS. 3A-3B and 5A-5B show the access port 19 on the apex (i.e., the hole in the bottom of the device) which is useful for implantation and for removing fluid that could accumulate between the heart and device. Additionally, a biocompatible lubricant, anti-clotting, anti-fibrosis, pharmaceuticals, or antibiotic agent may be injected into the space between the heart and device. So that the device may be removed easily after weaning, the device may be covered with a film that retards fibrous adhesions such as SURGI-WRAP®.

As noted above, because the RV operates at a lower pressure and has a thin wall, certain diastolic recoil devices of the present invention will enhance RV ejection more than LV ejection. As observed in the implantation of a prototype, driving pressures that are equal to or greater than pulmonary artery pressure may occur, resulting in a 100% RV ejection fraction is expected. Pulmonary congestion may result if RV output is continuously increased relative to LV output. Autoregulatory mechanisms may mitigate this enhancement of RV ejection over LV ejection. If not, separation of RV and LV chambers in the diastolic recoil device may be useful. In particular, it may be possible to impede RV filling with residual pressurization of the 4 RV chambers during diastole. By controlling input to the RV the ratio of RV output to LV output can be modulated.

Figures 6A, 6B:
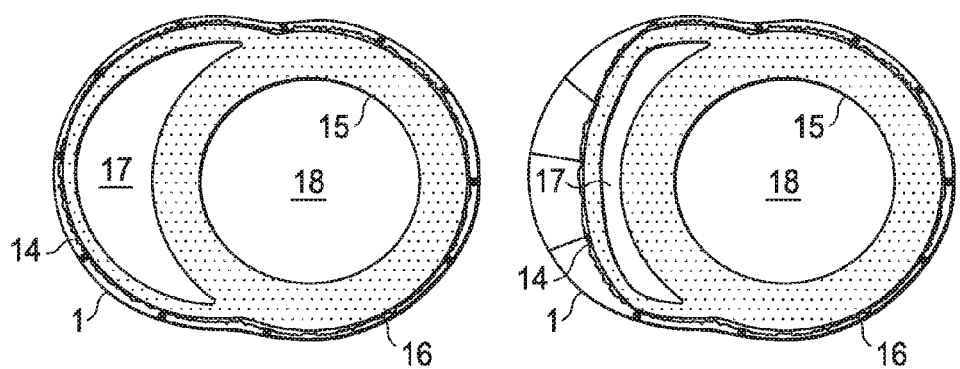
FIGS. 6A-6B are schematic diagrams of one embodiment of the present invention configured to reduce right ventricle input by reducing right ventricle filling.

FIGS. 6A and 6B illustrate how RV input (i.e., filling) can be modulated by the application of residual RV epicardial pressure (RRVEP). During diastole, the myocardium is relaxed and the heart shape is easy to perturb. This is particularly true of the RV freewall because it is very thin. Hence, residual gas in the four chambers abutting the RV freewall will likely prevent the RV from filling while leaving the LV unperturbed. It is, in essence, easier to differentially modulate filling than to modulate ejection.

FIGS. 6A and 6B illustrate a horizontal cross-section of one embodiment of the DCCD 1 of the present invention fitted to the heart 15. FIG. 6A is in the deflated state and FIG. 6B is in the inflated state. The DCCD 1 includes 12 chambers 2-13 arranged with 4 chambers on the RV side and 8 chambers that are mostly on the LV but also overlapping the interventricular sulci. The chambers 2-13 include interior surface 14 that contacts the epicardium 16 of the heart 15. The side of the chambers 2-13 that are on the outer boundary form a shape that is similar to the end diastolic shape of the heart. The interior surface 14 has folds and crenulations such that when inflated the chambers 2-13 mostly expand inward. The shape of the interior regions 17 and 18 can be compared in the inflated state as seen in FIG. 6B and the deflated state as seen in FIG. 6A.

The present invention overcomes the disadvantage of the potential RV freewall atrophying as a result of the RV volume being chronically decreased and native RV stroke work being decreased. Advantageously, the present invention proactively modulates the strain pattern, which is ideal for weaning the heart from a device because assist can be graded. Conventional DCCDs only assist when the heart is weak enough to be grossly deformed.

At end-systole of the cardiac cycle, the present invention has a shape with curvatures that are similar to the proper end-systolic shape of the heart. The present invention is active in the sense that energy is consumed to accomplish the shape change during systole and energy is liberated to accomplish the shape change during diastole. The energy source is from a pneumatic pressure source. During systole (i.e., shape change from end-diastole to end-systole) the device is inflated with a positive pressure. During diastole (i.e., shape change from end-systole to end-diastole) the device of the present invention is deflated via suction. If enabled for RV flow restriction, the device of the present invention is not fully deflated during diastole because some residual pressure is applied to chambers that abut the right ventricle.

The present invention is soft or collapsible when deflated. In addition, the present invention minimizes the risks of thrombosis and infection, as there is no contact with the blood. Many of the devices in the art when pressurized or the end-systolic shape of prior devices is grossly abnormal and this is evidenced by the various schemes used to attach the DCCD to the heart (e.g., sewing to ventricle, basal drawstring, apical suction cup, etc.).

There is no need to attach the present invention to the heart because the heart is naturally drawn into the pressurized or activated device. Specifically, for the heart to leave the device (i.e., be extruded from the diastolic recoil device), the device curvature would need to invert, yet the device rigidity (when pressurized) resists curvature inversion. This is very useful because implantation time and complications due to attachment are minimized when this feature is present—i.e., when the activated shape of the device cavity (i.e., the inner wall of the diastolic recoil device which touches the epicardial or outer boundary of the heart) is nearly end-systolic shape. It can eliminate dyskinesis (defined as abnormal cardiac motions). Current evidence indicates that differentiation of cardiac stem cells into functional cardiomyocytes is influenced by mechanical stimuli such as the motion during cardiac contraction whereby the elimination of dyskinesis is of paramount importance. The device provides some of the pumping power demanded of the heart to energize or pressurize the circulatory system. Abnormal hearts often need to be "off-loaded" or be assisted with satisfying the circulatory demands of the body.

FIG. 7 is an illustration of one embodiment of the present invention wherein a nitinol scaffold is incorporated to mediate the end-diastolic configuration.

FIGS. 8A and 8B are an illustration of two views of one embodiment of the present invention wherein a nitinol scaffold is incorporated to mediate the end-diastolic configuration.

The present invention comprises a biphasic and dynamic support device as illustrated in FIG. 9.

Figure 10:
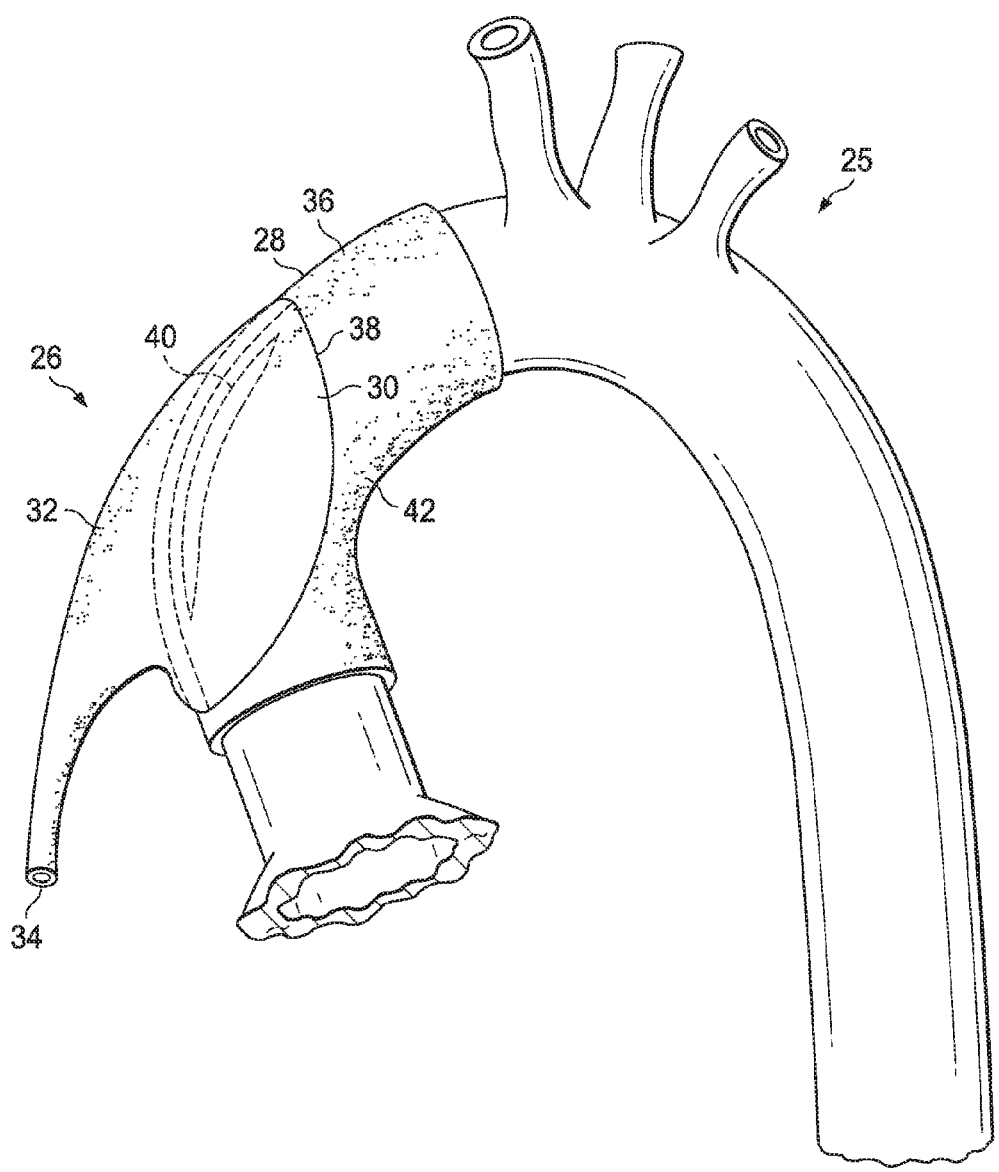
FIG. 10 shows a side view illustration of one embodiment of the implantable ascending aortic compression device of the present invention.

The present invention provides a fully implantable aortic compression device in communication with the direct cardiac compression device. FIG. 10 shows an illustration of a side view of one embodiment of the implantable aortic compression device of the present invention. FIG. 10 shows the ascending aorta 25 and the aortic compression device 26. The aortic compression device 26 has a relatively inelastic shell 28 (e.g., polymer, composite, plastic) sealed to and in operable communication with a flexible membrane 30. The flexible membrane 30 is separated from the inelastic shell 28 by an inflatable space to form an aorta compression chamber 32. The inelastic shell 28 includes an inlet/outlet port 34 which is adapted for connection to a fluid driver (not shown) that can systematically introduce and withdraw a fluid (e.g., a gas or a liquid) to and from the aorta compression chamber 32 in counterpulsation with the heart rhythm. The flexible membrane 30 has a shape which is, when deflated, smoothly curved and facing directly inwardly towards the lumen of the ascending aorta 25. The aortic compression device 26 is positioned about the ascending aorta 25 and may be connected using various methods including a relatively inelastic wrap 36 that is used to hold the aortic compression device 26 in position on the radially outer side of the ascending aorta 25.

In operation, when the aorta compression chamber 32 is deflated the flexible membrane 30 also deflates and does not deform the radially outer external aortic side wall 40. The flexible membrane 30 is shown relative to the inelastic shell 28 when the fluid has been withdrawn from the aorta compression chamber 32 and the flexible membrane 30 has been relaxed. In this position, the radially outer external aortic side wall 40 is in its normal or uncompressed position to allow unimpeded blood flow through the ascending aorta 25 for maximum blood flow. When the aorta compression chamber 32 is inflated through the addition of a fluid the flexible membrane 30 expands to an expanded membrane position 38 which in turn compresses the radially outer external aortic side wall 40 deforming it inwardly. The degree of deformation may be controlled from partially closed to mostly closed by adjusting the pressure such that the aorta compression chamber 32 compresses and inwardly deforms the radially outer external aortic side wall 40 until it is close to, but not abutting, the opposite aorta interior wall 42.

The flexible membrane 30 is sized and positioned to compress a portion of the circumference of the radially outer external aortic side wall 40. The flexible membrane 30 may compress from 100 to 200 degrees of the circumference of the aorta 25, e.g., about 120, 125, 130, 135, 140, 145, 150, and 155 degrees of the circumference of the aorta 25 and includes incremental variations thereof. In one specific embodiment the flexible membrane 30 is sized and positioned to compress only about 140 degrees of the circumference of the radially outer external aortic side wall 40.

The present invention includes an aortic compression device attached to the ascending (as shown) or descending (not shown) portion of the aortic wall and configured for external compression of the aortic wall so as when inflated to displace a certain volume of aortic blood flow for the purposes of causing a counterpulsation effect. Inflation of the aortic compression chamber may be done by injecting a drive fluid thereto using the driver.

Figure 11:
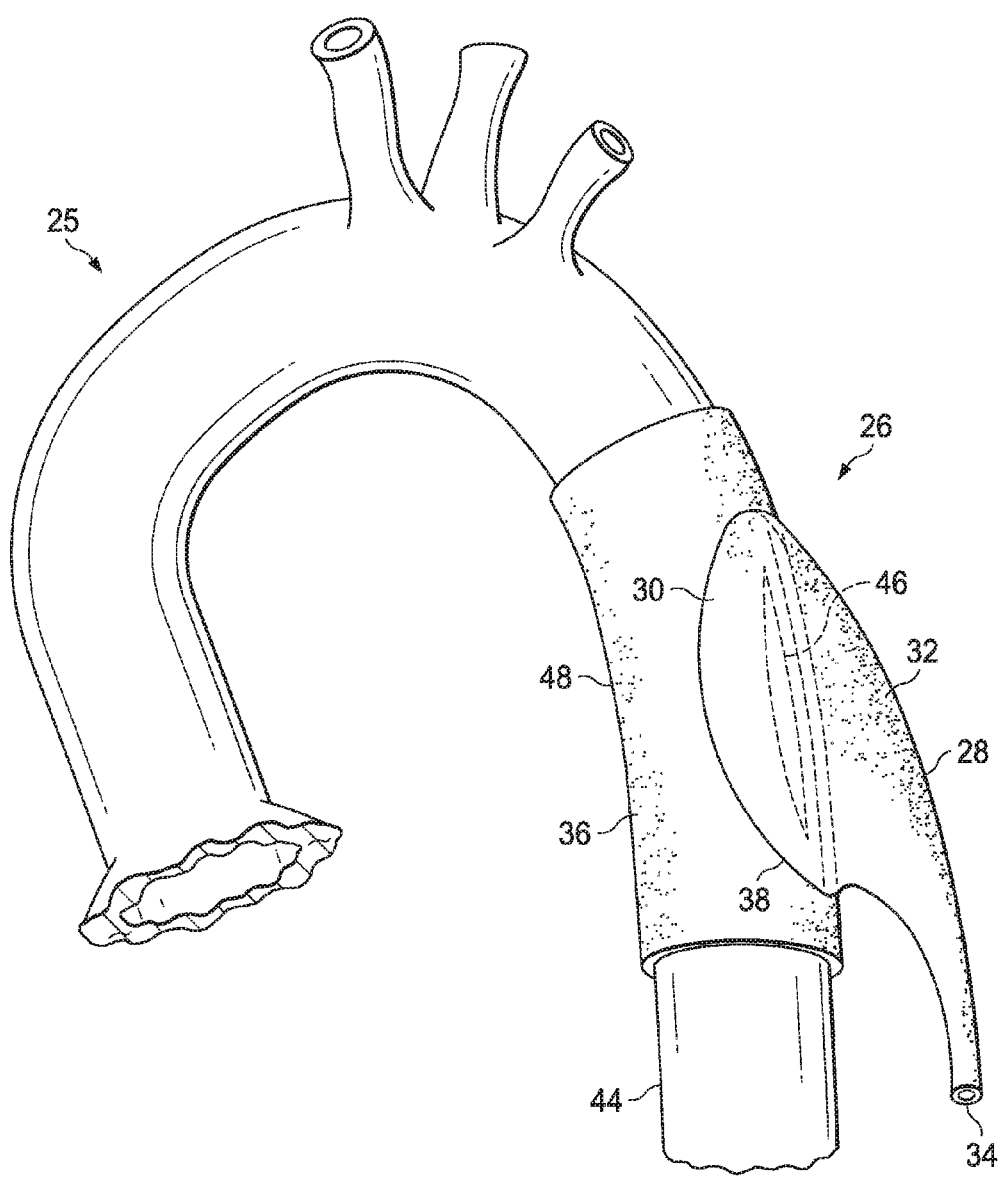
FIG. 11 shows a side view illustration of one embodiment of the implantable descending aortic compression device of the present invention.

The present invention provides a fully implantable descending aortic compression device in communication with the direct cardiac compression device. FIG. 11 shows an illustration of a side view of one embodiment of the implantable descending aortic compression device of the present invention. FIG. 11 shows the descending aorta 44 and the aortic compression device 26. The aortic compression device 26 has a relatively inelastic shell 28 (e.g., polymer, composite, plastic) sealed to and in operable communication with a flexible membrane 30. The flexible membrane 30 is separated from the inelastic shell 28 by an inflatable space to form an aorta compression chamber 32. The inelastic shell 28 includes an inlet/outlet port 34 which is adapted for connection to a fluid driver (not shown) that can systematically introduce and withdraw a fluid (e.g., a gas or a liquid) to and from the aorta compression chamber 32 in counterpulsation with the heart rhythm. The flexible membrane 30 has a shape which is, when deflated, smoothly curved and facing directly inwardly towards the lumen of the descending aorta 44. The aortic compression device 26 is positioned about the descending aorta 44 and may be connected with various methods including a relatively inelastic wrap 36 that is wrapped to hold the aortic compression device 26 in position on the radially outer side of the descending aorta 44.

In operation, when the aorta compression chamber 32 is deflated the flexible membrane 30 also deflated and does not deform the radially outer external descending aortic side wall 46. The flexible membrane 30 is shown relative to the inelastic shell 28 when the fluid has been withdrawn from the aorta compression chamber 32 and the flexible membrane 30 has been relaxed. In this position the radially outer external descending aortic side wall 46 is in its normal or uncompressed position, to allow unimpeded blood flow through the descending aorta 25 for maximum blood flow. When the aorta compression chamber 32 is inflated through the addition of a fluid, the flexible membrane 30 expands to an expanded membrane position 38 which in turn compresses the radially outer external descending aortic side wall 46 deforming it inwardly. The degree of deformation may be controlled from partially closed to mostly closed by adjusting the pressure so that the aorta compression chamber 32 inwardly deforms the radially outer external descending aortic side wall 46 until it is close to, but not abutting, the opposite descending aorta interior wall 48.

Figure 12:
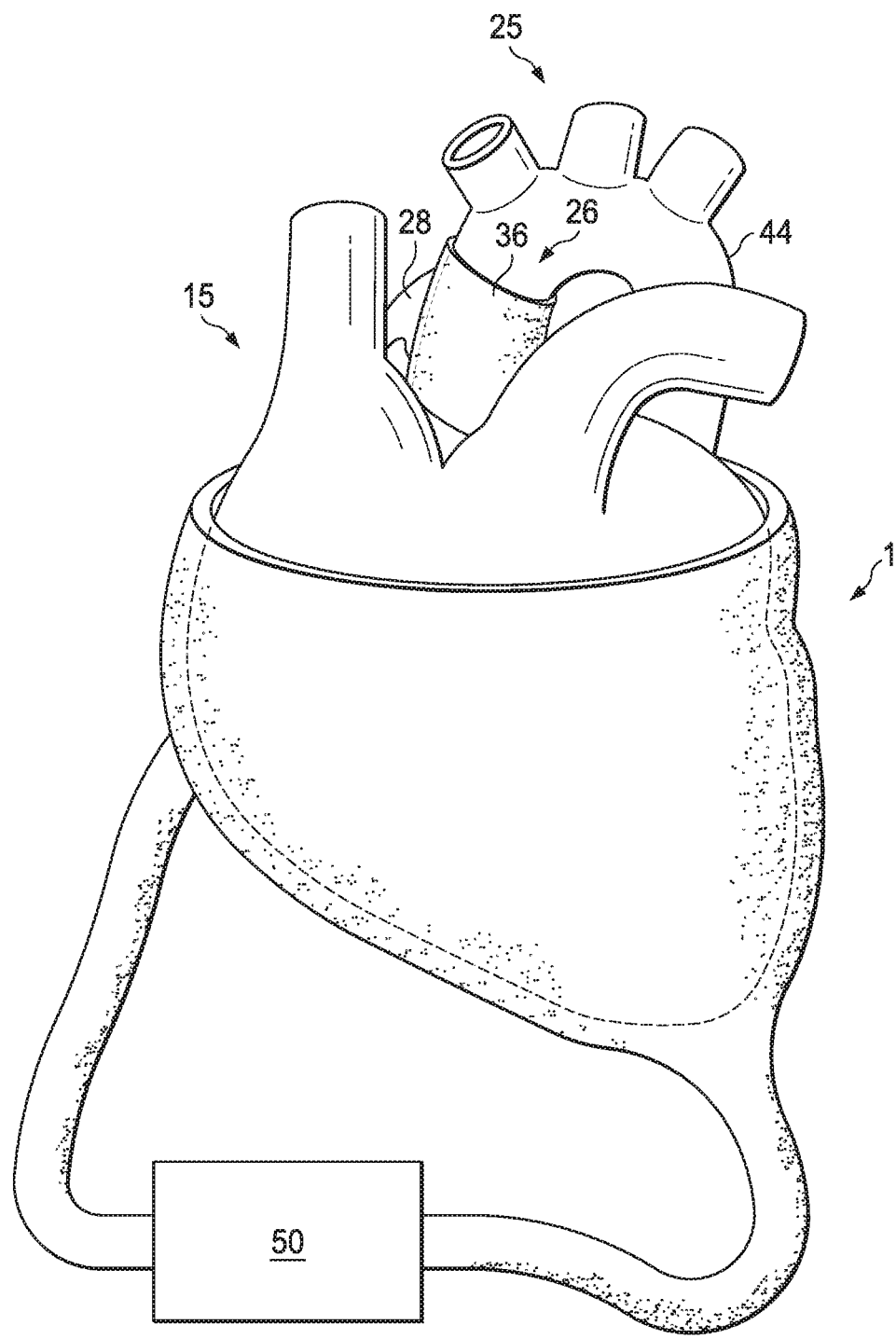
FIG. 12 illustrates one embodiment of the cardiac device of the present invention that includes a direct cardiac compression device and an aortic compression device.

FIG. 12 illustrates one embodiment of DCCD of the present invention that includes a DCCD and an aortic compression device. The DCCD 1 is fitted to the heart 15. The DCCD 1 includes inflatable chambers arranged with chambers on the RV side and chambers that are mostly on the LV but also overlapping the interventricular sulci. The chambers (not shown) include interior surface (not shown) that contacts the epicardium (not shown) of the heart 15. The side of the chambers (not shown) that are on the outer boundary form a shape that is similar to the end diastolic shape of the heart 15. The inflatable chambers taper as they go from base to apex in a manner that resembles natural cardiac curvature as seen in FIG. 3B, the apex of the heart 15 will have a physiological curvature. The interior surface (not shown) has folds and crenulations (not shown) such that when inflated the chambers (not shown) mostly expand inward. Moreover, because the DCCD 1 is rigid when pressurized, the curved shape of the apical end (not shown) will act to prevent the heart 15 from being expelled from the DCCD 1. Basically, for the heart 15 to leave the DCCD 1 the apical shape would have to pucker or a vacuum would need to form in the apical end of the DCCD 1, both of which are unlikely. A fluid driver 50 is in operable communication with the direct cardiac compression device 1 and the aortic compression device 26. One or more pressure regulators (not shown) may be included to regulate the pressure between the fluid driver 50 and the DCCD 1 and/or the fluid driver 50 and the aortic compression device 26. In addition, the fluid driver 50 may be in communication with a fluid reservoir (not shown) and/or a power supply (not shown), a motor (not shown), controller (not shown), and/or pacemaker. The aortic compression device 26 is connected to the ascending aorta 25 and includes a relatively inelastic shell 28 sealed in operable communication with a flexible membrane (not shown). The flexible membrane (not shown) is separated from the inelastic shell 28 by an inflatable space to form an aorta compression chamber (not shown). The inelastic shell 28 includes an inlet/outlet port (not shown) which is adapted for connection to the fluid driver 50 that can systematically introduce and withdraw a fluid (not shown) to and from the aorta compression chamber (not shown) in counterpulsation with the heart rhythm. The flexible membrane (not shown) has a shape which is, when deflated, smoothly curved and facing directly inwardly towards the lumen of the ascending aorta 25. The aortic compression device 26 is positioned about the ascending aorta 25 and held in place with a relatively inelastic wrap 36 on the radially outer side of the ascending aorta 25.

The fluid driver 50 causes an incompressible, low viscosity, biocompatible fluid, (e.g., air or saline) to flow in rhythmic pulsatile fashion into the aortic compression device 26 and alternatingly into the direct cardiac compression device. The DCCD and the aortic compression device can be fully implantable within a patient to assist the beating of the patient's heart 15. The device can include an aortic compression device, aortic compression device 26, a fluid reservoir, a pump, a motor, control unit, sensor, regulator, power supply and pacemaker (not shown) and can be fully or partially implantable subcutaneously in either the left or right chest or the upper abdomen.

The fluid driver 50 can be connected to a fluid reservoir (not shown) and controlled by a microprocessor in communication with one or more sensors that monitor and/or regulate the heart. In some embodiments, one or more check valves are in communication with the fluid driver 50. The DCCD, aortic compression device 26, fluid driver 50 and the fluid reservoir can each be constructed of at least one layer of material that is leak-proof, impermeable, and self-sealing. A prime volume of the fluid reservoir (not shown) can be predetermined based on a size of the patient and the fluid reservoir (not shown) can include an additional fluid volume to adjust hemodynamics. The fluid driver 50 can include a pump (not shown) directly attached to the motor or a pump remotely connected to a motor. The pump (not shown) can include a length of about three centimeters to about four centimeters and a diameter of about five centimeters, e.g., a length of 3.4 cm and a diameter of 5 cm. The pump (not shown) can use exotic materials including high purity thermoplastic. The pump (not shown) can include one or more impellars and a shaft constructed of a material including ceramic. In some embodiments, the motor (not shown) is a servo brushless direct current motor with a high starting torque and with a configuration to allow more space for coil winding. For example, the motor (not shown) can be a Series 1717 SR direct current micromotor with a precious metal commutator for use with a Series 16A spur gearhead, both manufactured by Faulhaber. The motor (not shown) can be powered by a rechargeable battery. In some embodiments, the battery can be externally recharged by radio frequency through a coil external to the patient. The fluid driver (not shown) can operate according to one or more of the following parameters: a normal voltage of about 1 Volts to about 8 Volts, a power output of about 1-4 Watts, an efficiency of about 50-90 percent, and a maximum recommended speed of from 500 to 5000 revolutions per minute. The fluid volume to inflate and deflate the aortic compression device and the direct cardiac compression device can be controlled by the speed of the fluid driver (not shown). Changing the speed of the motor 18 and the amount of fluid delivered, can allow adjustment of systolic pressure and can augment the function of the ventricles (not shown). Response to changing hemodynamic parameters can be in real time.

The control unit (not shown) can regulate compression of the heart 15 by the aortic compression device and the direct cardiac compression device through communication with the pacemaker and the fluid driver. For example, a synchronized pacemaker (not shown) can regulate pulsatility of the compressions or the aortic compression device and the direct cardiac compression device. The control unit can regulate the compression and the decompression of the heart by the direct cardiac compression device. Synchronization by the control unit through communication with the pacemaker and the fluid driver can be based on dual-mode, dual-pacing, dual-sensing pacing, biventricular pacing, and/or three-chamber synchronization pacing. Pulsation ratios of inflation and deflation of the aortic compression device and the direct cardiac compression device can be adjusted on the basis of cardiac parameters, and the severity of the heart condition. A lower pulsation ratio can extend use of the rechargeable battery powering the control unit, sensors, fluid driver, pump, motor, and/or pacemaker. The pacemaker (not shown) can monitor the heart 15 with one or more leads coupled to one or more of the right ventricle, the left ventricle, the right atrium, and the left atrium. The pacemaker (not shown) can be part of the control unit and include a processor that determines left ventricular cardiac parameters and right ventricular cardiac parameters. The cardiac parameters can include one or more of the following: left ventricular end diastolic pressure (LVEDP), left ventricular end systolic pressure (LVESP), right ventricular end diastolic pressure (RVEDP), right ventricular end systolic pressure (RVESP), left ventricular volume, right ventricular volume, cardiac tension, cardiac output, systolic blood pressure, diastolic blood pressure, and heart rate. The pacemaker can respond to changes in the cardiac parameters by changing the inflation rate, the deflation rate, and/or the fluid volume. In some embodiments, the pacemaker can continuously monitor and regulate cardiac hemodynamics in real time. The monitoring and regulating can be continuous and can immediately respond to changing cardiac hemodynamics. The pacemaker and/or control unit (not shown) can be programmed for mild, moderate, or severe heart disease.

Some embodiments of the invention include a device that is completely implantable, there is no interface with blood components that could cause coagulopathy or related morbidity, the patient can be completely ambulatory and physically active with the device implanted thus contributing to the quality of life, and expensive external monitoring to adjust the compression pressure is not required. Some embodiments of the invention respond to changing hemodynamics, which are constantly monitored. Embodiments of the invention are also cost effective in terms of initial insertions costs, subsequent hospitalizations, and follow-up costs.

The speed of fluid driver (which may include a kinetic or centrifugal pump, a peristaltic or positive displacement pump but may be of any type including axial turbine or a radial pump (not shown)) may be coordinated with pressure regulator to create a sequence or series of wave forms or pulses of fluid in direct cardiac compression device to be rhythmically massaged or compressed. The regulation of pressures may be achieved by a relief valve coupled to the fluid circuit, a pressure regulator, or possibly, by "pump surge." Pressure regulator and pump are electrically coupled to a controller means or module, e.g., a microprocessor. The intensity of the compression step can be adjusted by adjusting the fluid driver, pump, pump speed and/or pressure regulator.

The combined device of the invention takes advantage of the opposite timing of the cardiac and aortic compressions to shuttle the drive fluid back and forth in between the aortic compression device and the direct cardiac compression device. This approach inherently solves the issue of dead space and expanding driver as described above.

ECG-based or other heart event triggers are envisioned to be a part of the system (not shown) configured to provide the controller with reliable predictive or real-time information about the expected timing of systole and diastole of the heart.

The device may be battery-operated or be supported by an external electrical energy transmitted across the skin using TET transmission coupling (not shown).

In its simplest operation mode, the driver may include an impeller, which is configured to first inflate the cardiac compression chamber at the beginning of systole by injecting drive fluid thereto. The drive fluid is removed from the aortic compression chamber causing it to collapse and reduce aortic pressure momentarily so as to assist the heart muscle. The systole of the heart will be therefore accompanied by both the compression of the heart muscle externally as well as by reduced aortic pressure to make it easier for the muscle to eject blood therefrom. During diastole of the heart, the impeller may be reversed to cause deflation of the cardiac compression chamber and inflation of the aortic compression chamber. That action will cause a momentary increase in aortic pressure, which may help to increase coronary blood flow—another helpful effect of the device of the present invention. In case of power failure, the system may be configured to deflate the cardiac compression bladders and inflate the aortic compression bladder. This will remove the restriction on heart movement but at the same time will not create a significant flow obstruction in the aorta.

Figure 13:
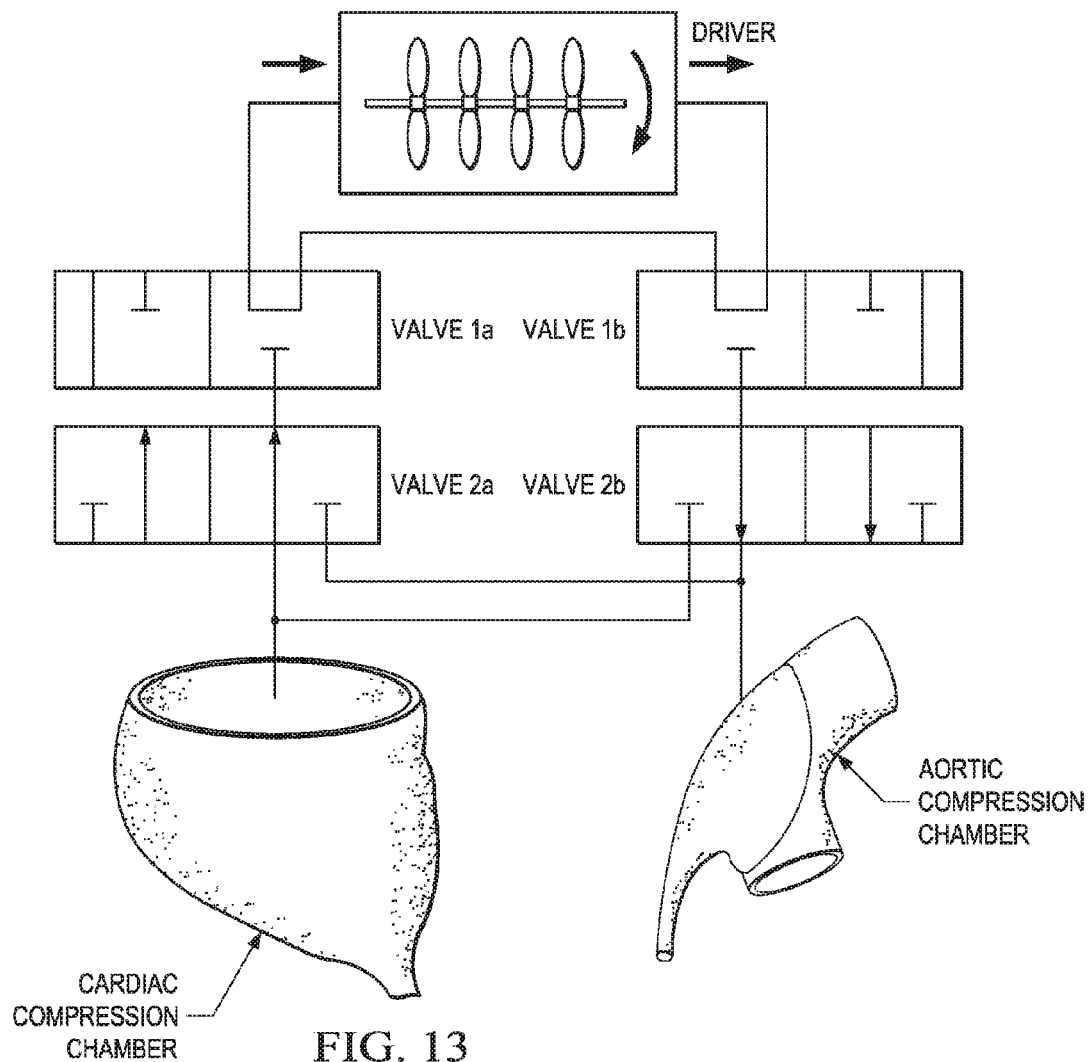
FIG. 13 illustrates another embodiment of the cardiac device of the present invention that includes a direct cardiac compression device and an aortic compression device.

FIG. 13 illustrates another embodiment of the cardiac device of the present invention that includes a direct cardiac compression device and an aortic compression device. This system allows for a more sophisticated timing to be employed. Inflation and deflation of both chambers is desirable to be complete in the shortest time possible. Inertia of the rotating impeller may inhibit its fast reversal. To solve this problem, the device uses an impeller configured to rotate continuously in the same direction. A system of valves may be used to reverse the direction of the flow as well as to pause the flow of the drive fluid—without changing the direction or the speed of rotation of the impeller. The duration of systole as well as diastole may be longer than the time required to shift the volume of fluid from one chamber to the other. In order to unload the driver from having to exert continuous pressure and reduce the energy consumption, valves $1a$ and $1b$ are proposed to be included and configured to isolate the impeller from the chambers and the chambers from each other. Shifting valves $1a$ and $1b$ will reconnect the impeller to the chambers and allow the next phase of operation. Valves $2a$ and $2b$ are configured to reverse the direction of flow between the two compression chambers in order to reciprocate the drive fluid back and forth between the cardiac compression and the aortic compression chambers—while maintaining the rotation of the impeller in the same direction. Aortic compression chamber may also include an inflatable chamber positioned inside the aorta and configured when inflated to displace aortic volume and provide the same counterpulsation effect as the traditional intra-aortic balloon pump.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A combined direct cardiac compression and aortic counterpulsation device comprising:
    an inflatable direct cardiac compression jacket configured when inflated to directly compress a heart and assist in displacing blood therefrom, wherein the inflatable direct cardiac compression jacket comprises an inner membrane attached to an outer member and contoured to surround a heart to compresses the heart during contraction without inverting or significantly perturbing the curvatures of the heart and a fluid between the outer member and the inner membrane, wherein and the device exerts a non-curvature-inverting contraction stain pattern when used on a heart, when the fluid is pressurized;
    an aortic counterpulsation chamber configured when inflated to displace aortic volume for the purposes of causing a counterpulsation effect, and
    a driver operably connected to said inflatable direct cardiac compression jacket and to said aortic counterpulsation chamber, said driver is configured to move the fluid to inflate said direct cardiac compression jacket and to deflate said aortic counterpulsation chamber during systole of the heart; said driver is further configured to deflate said direct cardiac compression jacket and to inflate said aortic counterpulsation chamber during diastole of the heart.

2. A combined direct cardiac compression and aortic counterpulsation device comprising:
    an inflatable direct cardiac compression jacket configured when inflated to directly compress an external surface of a heart and assist in displacing blood therefrom,
    an aortic counterpulsation chamber configured when inflated to displace aortic volume for the purposes of causing a counterpulsation effect, and
    a driver operably connected to said inflatable direct cardiac compression jacket and to said aortic counterpulsation chamber, said driver is configured to shuttle a drive fluid back and forth between said direct cardiac compression jacket and said aortic counterpulsation chamber to alternate inflations and deflations thereof.

3. A combined direct pulsation and counterpulsation device comprising:
    a first inflatable component in direct contact with a heart,
    a second inflatable component in direct contact with at least one great artery,
    a driver operably connected to said first and second inflatable components, wherein said device is configured to fill said first inflatable component with fluid at least partially removed from said second inflatable component during systolic ejection by the heart; said device is further configured to fill said second inflatable component with fluid at least partially removed from said first inflatable component during diastolic filling of the heart.

4. A combined direct cardiac compression and aortic counterpulsation device comprising:
    an inflatable direct cardiac compression device comprising
    a resilient inner panel in contact with a heart periphery comprising one or membranes contoured to provide curvatures generally in the shape of the heart to supply resistance to the movement of the heart to affect the end-diastolic heart volume,
    an inflatable outer panel comprising one or more inflatable membranes positioned at least partially around the resilient inner panel to inflate and provide resistance to the movement of the heart to affect the end-systolic heart volume without inverting or significantly perturbing the curvatures of the heart, and one or more fluid connections in communication with the inflatable outer panel for inflation and deflation;
    an aortic counterpulsation device, wherein the aortic counterpulsation device comprises a shell comprising an outer surface and a substantially concave inner surface, a flexible membrane coupled to the shell to form an inflatable space therebetween, wherein the flexible membrane has a deflated configuration and an inflated configuration, an inlet/outlet port in fluid communication with the inflatable space, and coupled to the shell to removeably position to hold the flexible membrane against a radially outer side of a curvature of the aorta; and
    a driver operably connected to the one or more fluid connections of the inflatable direct cardiac compression device and to the aortic counterpulsation device to inflate the inflatable direct cardiac compression device and to deflate the aortic counterpulsation device during systole of the heart and to deflate the inflatable direct cardiac compression device and to inflate the aortic counterpulsation device during diastole of the heart.

5. The device of claim 4, wherein the aortic counterpulsation device comprises a wrap around the shell for holding the device against the ascending aorta, wherein the shell is configured to extend around only a portion of the circumference of the ascending aorta.

6. The device of claim 4, wherein the shell is a substantially inelastic curved shell.

7. The device of claim 4, wherein the flexible membrane is substantially inelastic.

8. The device of claim 4, wherein a fluid is disposed within the inflatable space in the inflated configuration.

9. The device of claim 4, wherein the concave inner surface forms a smooth curved ovate projection configured to cause the outer side of the curvature of the aorta to flex into a conic shape.

10. The device of claim 4, wherein the concave inner surface forms a smooth curved ovate projection configured to cause the outer side of the curvature of the aorta to flex substantially without stretching a wall of the aorta.

11. The device of claim 4, wherein the inflatable direct cardiac compression device comprises eight at least partially overlapped membranes connected to form a continuous outer edge.

12. The device of claim 4, wherein the resilient inner panel, the inflatable outer panel or both comprise an elastomeric polyurethane, a latex, a polyetherurethane, a polycarbonateurethane, a silicone, a polysiloxaneurethane, a hydrogenated polystyrene-butadiene copolymer, an ethylene-propylene, a dicyclopentadiene terpolymer, hydrogenated poly(styrene- butadiene) copolymer, a poly(tetramethylene-ether glycol) urethanes, a poly (hexamethylenecarbonate-ethylenecarbonate glycol) urethanes or combinations thereof.

13. The device of claim 4, further comprising one or more resilient members comprise individually a metal, an alloy, a memory metal, a composite, a polymer, a plastic, a memory plastic, strands, yarns, strips, or a combination thereof.

14. The device of claim 4, further comprising one or more sensors, one or more electrodes to provide pacing stimuli to the heart, one or more electrodes to provide an electrical shock to the heart for defibrillation, one or more electrodes to provide an electrical stimuli to the heart, or a combination thereof in contact with the direct compression cardiac device.

15. The device of claim 4, further comprising one or more bioactive agents selected from antimicrobials, antibiotics, antimitotics, antiproliferatives, antisecretory agents, non-steroidal anti-inflammatory drugs, immunosuppressive agents, antipolymerases, antiviral agents, antibody targeted therapy agents, prodrugs, free radical scavengers, antioxidants, biologic agents or combinations thereof.

16. The device of claim 4, wherein the driver is an electric driver.

17. The device of claim 4, wherein the inflatable direct cardiac compression device comprises an inner membrane attached to an outer member and contoured to surround a heart to compresses the heart during contraction without inverting or significantly perturbing the curvatures of the heart and a fluid between the outer member and the inner membrane, wherein and the device exerts a non-curvature-inverting contraction stain pattern when used on a heart, when the fluid is pressurized.

* * * * *